United States Patent
Chang et al.

(10) Patent No.: US 8,754,573 B2
(45) Date of Patent: Jun. 17, 2014

(54) ULTRASONIC TRANSDUCER DETECTOR WITH RESONANT UNIT HAVING A THICKNESS OF HALF-WAVELENGTH OF THE OPERATING FREQUENCY

(75) Inventors: Pin Chang, Hsinchu (TW); Feng-Chia Hsu, Kaohsiung County (TW); Di-Bao Wang, Tainan (TW); Chin-Hung Wang, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 661 days.

(21) Appl. No.: 13/039,279

(22) Filed: Mar. 2, 2011

(65) Prior Publication Data

US 2012/0146458 A1 Jun. 14, 2012

(30) Foreign Application Priority Data

Dec. 14, 2010 (TW) .............................. 99143759 A

(51) Int. Cl.
*H01L 41/08* (2006.01)
*B06B 1/06* (2006.01)

(52) U.S. Cl.
CPC ...................................... *B06B 1/064* (2013.01)
USPC ............................ 310/334; 600/437; 600/459

(58) Field of Classification Search
USPC ................................... 310/334; 600/437, 459
See application file for complete search history.

(56) References Cited

U.S. PATENT DOCUMENTS

| | | | |
|---|---|---|---|
| 6,645,150 B2 | 11/2003 | Angelsen et al. | |
| 6,659,954 B2 | 12/2003 | Robinson | |
| 7,449,821 B2 | 11/2008 | Dausch | |
| 7,982,369 B2 * | 7/2011 | Ona et al. ...................... | 310/334 |
| 2010/0168583 A1 | 7/2010 | Dausch et al. | |

FOREIGN PATENT DOCUMENTS

| | | |
|---|---|---|
| CN | 1990063 | 7/2007 |
| CN | 101524283 | 9/2009 |
| TW | 200821052 | 5/2008 |

OTHER PUBLICATIONS

"Office Action of Taiwan counterpart application" issued on Jul. 18, 2013, p. 1-p. 6.
Brown et al., "Design and Fabrication of Annular Arrays for High-Frequency Ultrasound," IEEE Transactions on Ultrasonics, Ferroelectrics, and Frequency Control, vol. 51, No. 8, p. 110-p. 1017, Aug. 2004.
Cannata et al., "Development of a 35-MHz Piezo-Composite Ultrasound Array for Medical Imaging," IEEE Transactions on Ultrasonics, Ferroelectrics, and Frequency Control, vol. 53, No. 1, p. 224-p. 236, Jan. 2006.
Dorey et al., "Fabrication and Characterization of Annular Thickness Mode Piezoelectric Micro Ultrasonic Transducers," IEEE Transactions on Ultrasonics, Ferroelectrics, and Frequency Control, vol. 54, No. 12, p. 2462-p. 2468, Dec. 2007.

(Continued)

*Primary Examiner* — J. San Martin
(74) *Attorney, Agent, or Firm* — Jianq Chyun IP Office

(57) ABSTRACT

An ultrasonic transducer detector having a high operating frequency is provided. The ultrasonic transducer detector comprises a substrate and an ultrasonic transducer array. The substrate has a plurality of openings, and the ultrasonic transducer array is disposed on the substrate. The ultrasonic transducer array has a plurality of resonance units, and the thickness of each resonance unit is equivalent to ½ wavelength of the operating frequency of the ultrasonic transducer. Each resonance unit comprises an oscillating element and a piezoelectric element. The oscillating element has a first surface adjacent to the substrate, and the piezoelectric element is disposed on the first surface and located in the corresponding opening.

10 Claims, 11 Drawing Sheets

(56) References Cited

OTHER PUBLICATIONS

Duval et al., "Fabrication and Modeling of High-Frequency PZT Composite Thick Film Membrane Resonators," IEEE Transactions on Ultrasonics, Ferroelectrics, and Frequency Control, vol. 51, No. 10, p. 1255-p. 1261, Oct. 2004.

Muralt et al., "Piezoelectric Micromachined Ultrasonic Transducers Based on PZT Thin Films," IEEE Transactions on Ultrasonics, Ferroelectrics, and Frequency Control, vol. 52, No. 12, p. 2276-p. 2288, Dec. 2005.

"Office Action of China Counterpart Application", issued on Mar. 31, 2014, p. 1-p. 6, in which the listed references were cited.

* cited by examiner

ULTRASONIC TRANSDUCER DETECTOR WITH RESONANT UNIT HAVING A THICKNESS OF HALF-WAVELENGTH OF THE OPERATING FREQUENCY

CROSS-REFERENCE TO RELATED APPLICATION

This application claims the priority benefit of Taiwan application serial no. 99143759, filed Dec. 14, 2010. The entirety of the above-mentioned patent application is hereby incorporated by reference herein and made a part of this specification.

TECHNICAL FIELD

The invention relates to a detector, and more particularly to an ultrasonic transducer detector.

BACKGROUND

An ultrasonic non-invasive surgery has advantages of low risk, few side effects and allowing the patient to leave the hospital quickly afterward, and has been widely used in various medical fields. In order to expand the application scope of the ultrasonic non-invasive surgery, for example, being applied to the medical fields of micro-tissues such as cardiovascular surgery, ophthalmology or invasive sound therapy, a high-frequency and high-resolution ultrasonic array is under development.

In recently years, international research and development units introduce a Piezoelectric Micromachined Ultrasound Transducer (pMUTs) (referred to as pMUTs technology in the following) having high precision and wafer-level volume production. The pMUTs technology deposits a thin-film piezoelectric material (several μms) on a silicon substrate, and then defines an ultrasonic transducer element having an empty back-cavity through lithography, development and etching processes.

The current pMUTs technology uses a plane dimension defining the ultrasonic transducer element to obtain a flexure mode to determine an operating frequency of the piezoelectric ultrasonic detector. In practical application, many ultrasonic transducer units are usually gathered and arranged into an ultrasonic transducer array having a unit space between adjacent units. However, according to the above design, the unit space of the ultrasonic transducer array is usually greater than ½ wavelength of the operating frequency, and when the unit space is greater than ½ wavelength of the environment under test, a grating lobe effect as shown in FIGS. 1A and 1B is caused. To form an image of 0 degree, wrong reflection information with angles $\theta_1$ and $\theta_{-1}$ are thus generated, resulting in wrong radiography, and a real image of the object to be tested cannot be reliably obtained.

SUMMARY

An ultrasonic transducer detector with high operating frequency is introduced herein, which comprises a substrate and an ultrasonic transducer array. The substrate has a plurality of openings located on a first surface, and the ultrasonic transducer array is disposed on the first surface of the substrate. The ultrasonic transducer array has at least one resonance unit, and the thickness of each resonance unit is equivalent to ½ wavelength of the operating frequency. Each resonance unit comprises an oscillating element and a piezoelectric element. The oscillating element has a second surface adjacent to the substrate, the second surface corresponds to the opening on the first surface of the substrate, and the piezoelectric element is disposed on the second surface.

Several exemplary embodiments accompanied with figures are described in detail below to further describe the invention in details.

BRIEF DESCRIPTION OF THE DRAWINGS

The accompanying drawings are included to provide further understanding, and are incorporated in and constitute a part of this specification. The drawings illustrate exemplary embodiments and, together with the description, serve to explain the principles of the invention.

DETAILED DESCRIPTION OF DISCLOSED EMBODIMENTS

Figure 1A:
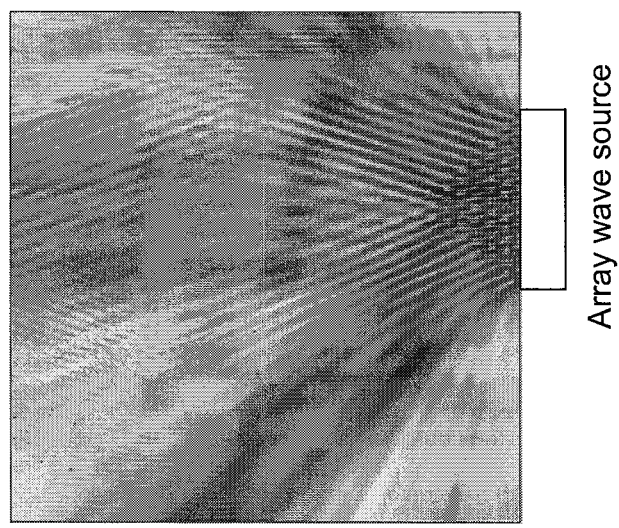
FIG. 1A is a simulated sound field diagram illustrating a pointing effect in water when the unit space between adjacent units of a wave source array is greater than ½ wavelength.
Figure 1B:
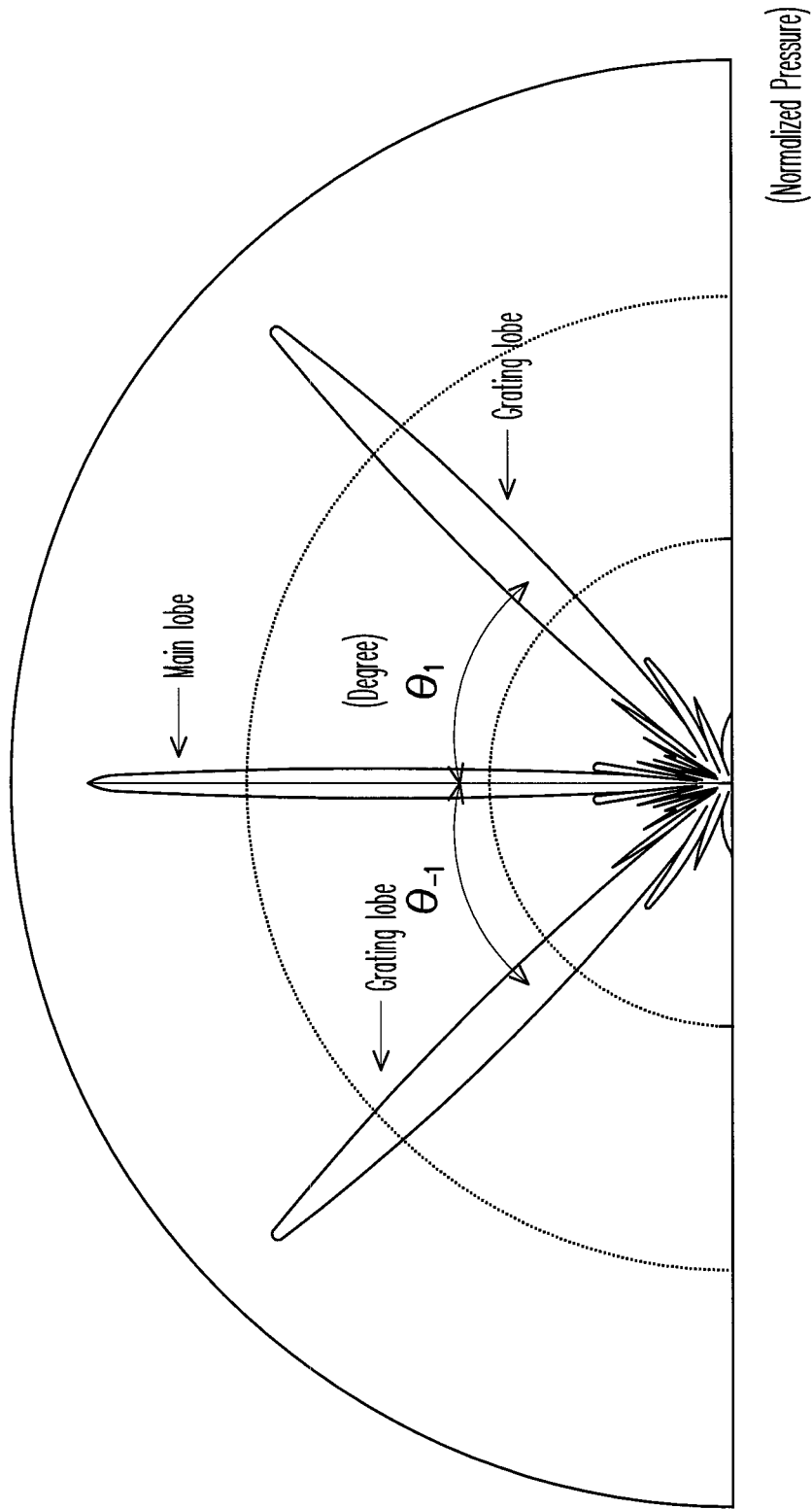
FIG. 1B is a schematic diagram illustrating a grating lobe effect.
Figure 2:
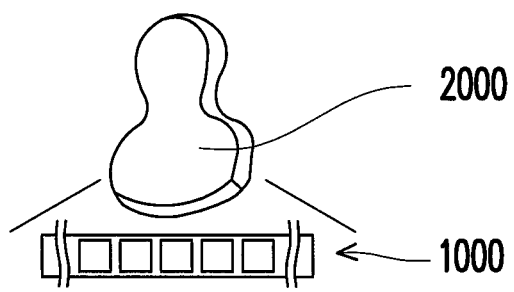
FIG. 2 is a schematic diagram illustrating an ultrasonic probe according to the invention.
Figure 2:
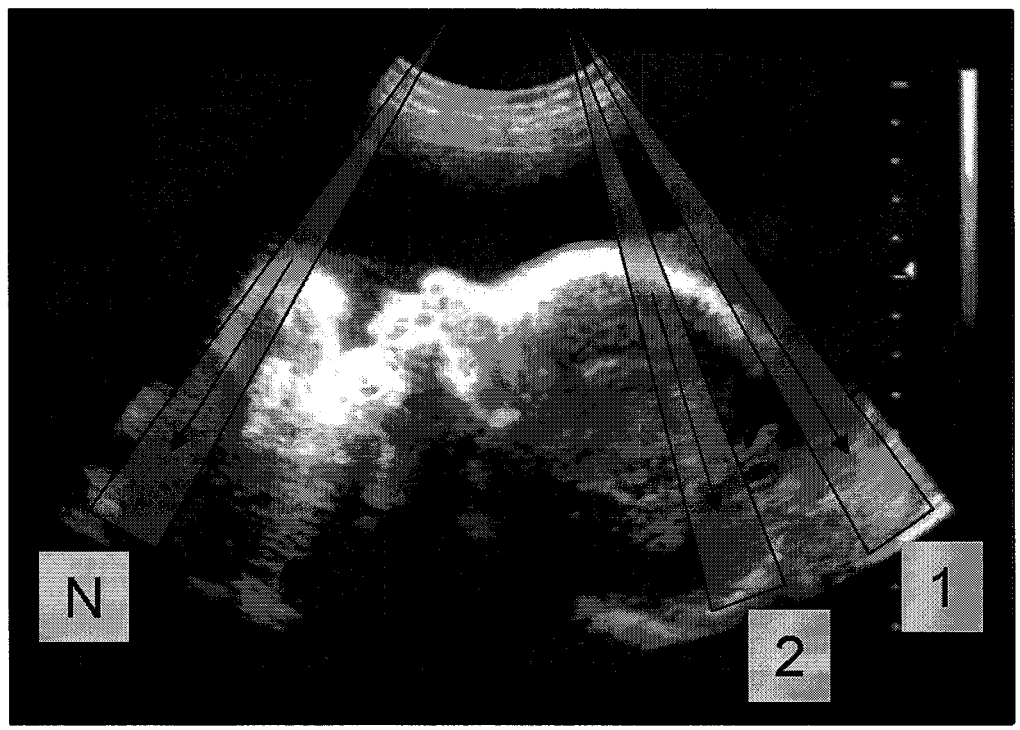
Figure 3:
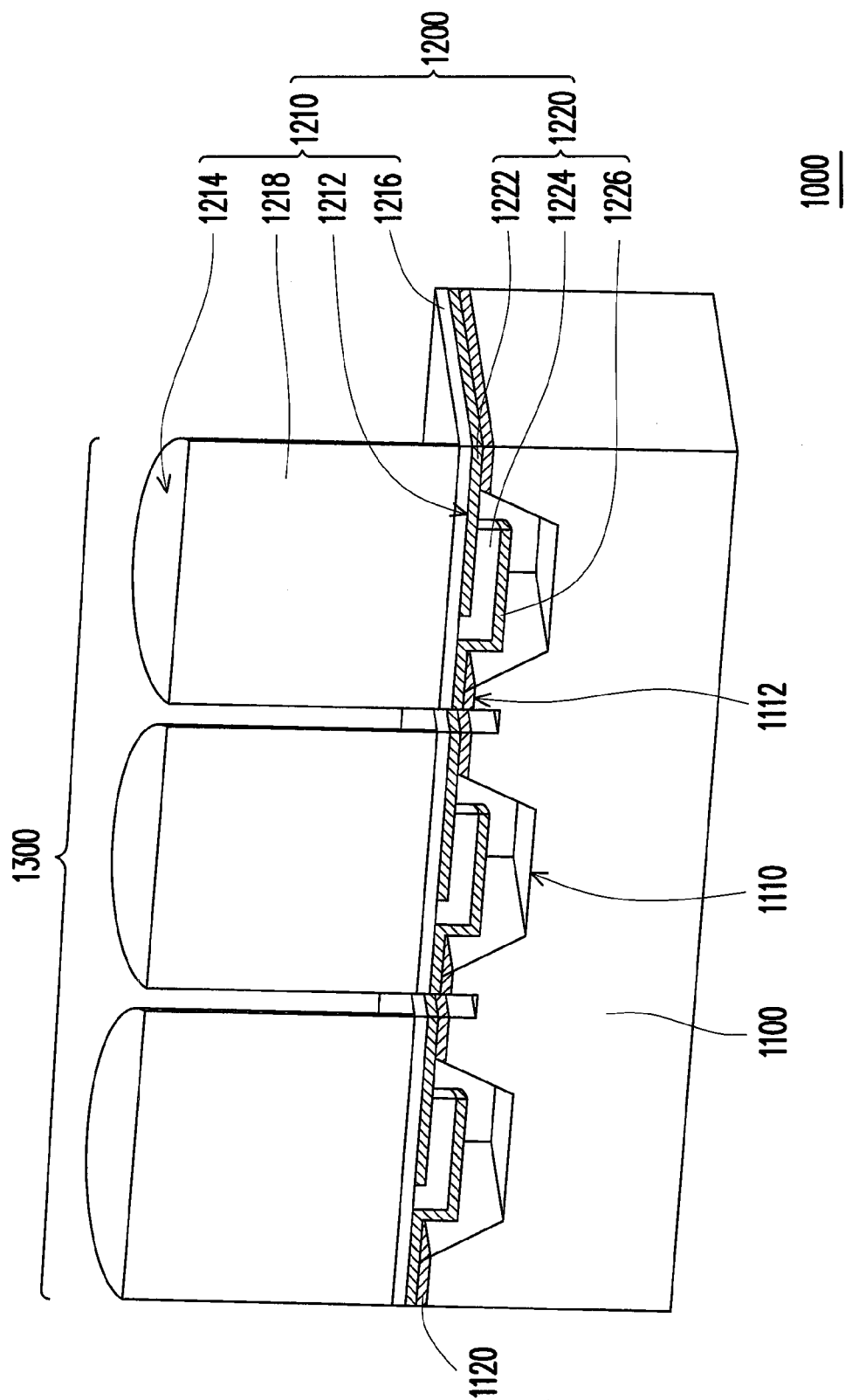
FIG. 3 is a schematic three-dimensional diagram illustrating a part of an ultrasonic transducer detector applied to the ultrasonic probe in FIG. 2.
Figure 4:
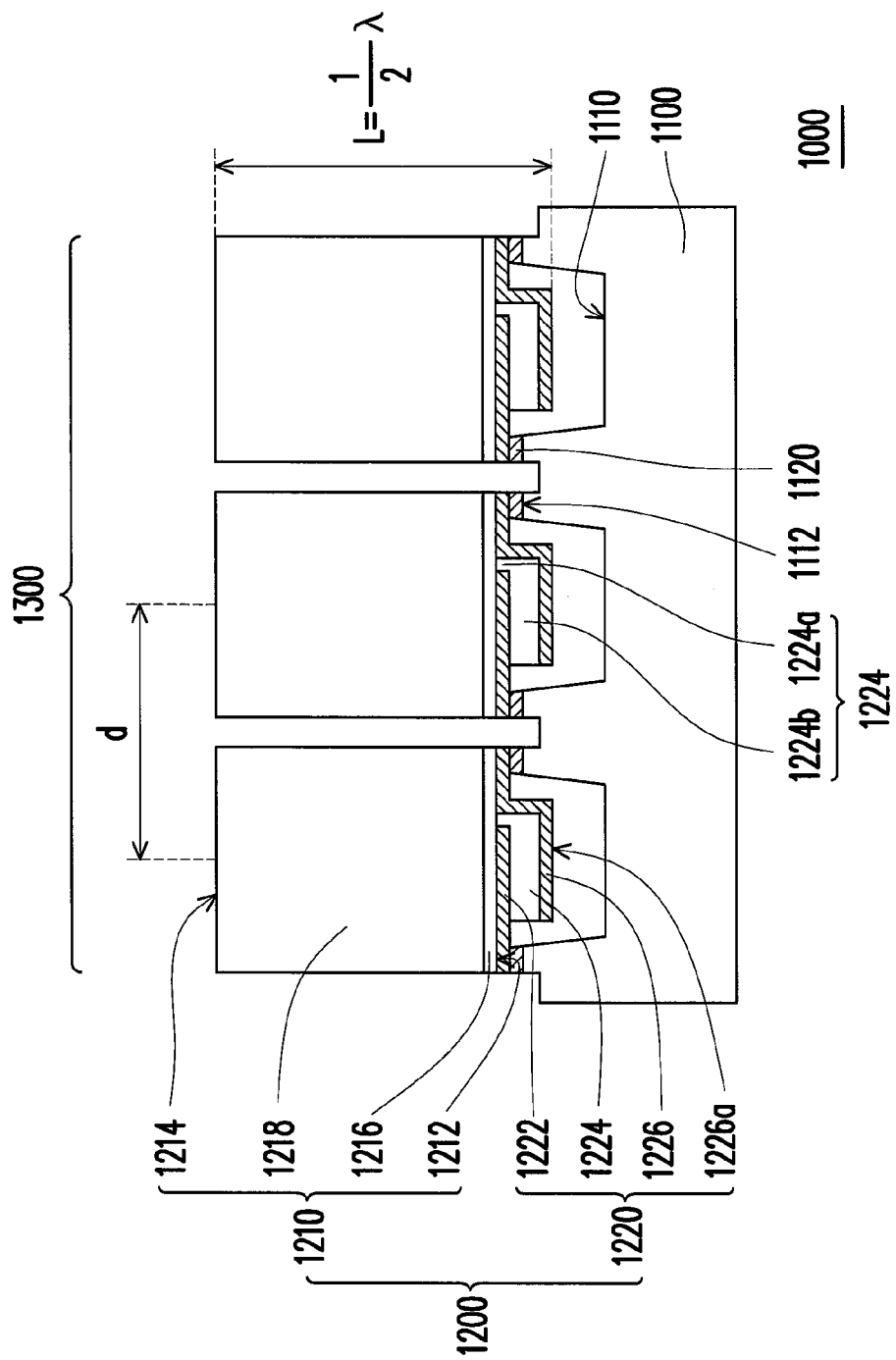
FIG. 4 is a schematic sectional diagram of FIG. 3.

FIG. 2 is an abdominal ultrasonography performed by an ultrasonic probe according to the invention, FIG. 3 is a schematic three-dimensional diagram illustrating a part of an ultrasonic transducer detector applied to the ultrasonic probe in FIG. 2, and FIG. 4 is a schematic sectional diagram of FIG. 3. Referring to FIGS. 2, 3, and 4, the ultrasonic transducer detector 1000 of this embodiment is applicable to the ultrasonic probe 2000 used in medical fields such as abdominal ultrasonography, ophthalmology, or cardiovascular surgery. The ultrasonic transducer detector 1000 has an operating frequency approximately between 25 MHz and 50 MHz, but may also be applied to the field with a frequency lower than 25 MHz or higher than 50 MHz. The ultrasonic transducer detector 1000 comprises a substrate 1100 and an ultrasonic transducer array 1300. The substrate 1100 has a plurality of openings 1110, the openings 1110 are located on a first surface 1112 of the substrate 1100, and the ultrasonic transducer array 1300 is disposed on the first surface 1112 of the substrate 1100. The ultrasonic transducer array 1300 has at least one resonance unit 1200, and the thickness L of each resonance unit 1200 is equivalent to ½ wavelength λ of the operating frequency F. Each resonance unit 1200 comprises an oscillating element 1210 and a piezoelectric element 1220. The oscillating element 1210 has a second surface 1212 adjacent to the substrate 1100, the second surface 1212 corresponds to the opening 1110 located on the first surface 1112 of the substrate 1100, and the piezoelectric element 1220 is disposed on the second surface 1212. In this embodiment, the thickness of the resonance unit 1200 of the ultrasonic transducer array 1300 in the ultrasonic transducer detector 1000 is used to determine the operating frequency of the ultrasonic transducer detector 1000; therefore, the plane dimension of the resonance unit 1200 can be reduced, to narrow the unit space between the adjacent units, inhibit the grating lobe effect, and generate radiography correctly.

Specifically, the substrate 1100 may be a silicon substrate having multiple semiconductor elements and a layout 1120 disposed thereon, and the resonance unit 1200 of the ultrasonic transducer array 1300 is electrically connected to the semiconductor elements through the layout 1120. Furthermore, in this embodiment, the openings 1110 of the substrate 1100 are blind holes not penetrating the substrate 1100; however, in other embodiments (not shown), the openings 1110 may also be through holes penetrating the substrate 1100.

The oscillating element 1210 comprises an insulating layer 1216 and an oscillating body 1218. The second surface 1212 is the surface of the insulating layer 1216 adjacent to the substrate 1100. The oscillating element 1210 is made of an elastic material, in which the insulating layer 1216 may be made of an oxide, and the oscillating body 1218 may be made of a metal or semiconductor material. Specifically, in this embodiment, the oscillating body 1218 is made of silicon. Furthermore, the oscillating body 1218 is a column, but the shape of which is not limited and may be a cylinder, a triangular prism, or a rectangular column. The shape of the oscillating body 1218 may be changed according to actual requirements.

Based on the above, each piezoelectric element 1220 comprises a first electrode 1222, a piezoelectric material layer 1224, and a second electrode 1226. The first electrode 1222 is disposed on the second surface 1212 of the oscillating element 1210, and the first electrode 1222 covers a part of the second surface 1212 and does not cover the entire second surface 1212. The piezoelectric material layer 1224 has a first part 1224a and a second part 1224b connected to each other. The first part 1224a is disposed on the second surface 1212 of the oscillating element 1210 and located next to the first electrode 1222; and the second part 1224b is disposed on the surface of the first electrode 1222. The second electrode 1226 comprises a part covering the second surface 1212 of the oscillating element 1210, a part exposed by the first electrode 1222 and the piezoelectric material layer 1224, and extending to be disposed on the piezoelectric material layer 1224. Therefore, the piezoelectric material layer 1224 is located between the first electrode 1222 and the second electrode 1226. Furthermore, each oscillating element 1210 has a third surface 1214 adjacent to the second surface 1212 and being away from the substrate 1100, and the second electrode 1226 has a fourth surface 1226a adjacent to the openings 1110. The thickness L of each resonance unit 1200 is a distance between the third surface 1214 of the oscillating element 1210 and the fourth surface 1226a of the second electrode 1226.

FIGS. 5A to 5F are flow charts illustrating a manufacturing process of the ultrasonic transducer detector. The manufacturing process of the ultrasonic transducer detector 1000 is described briefly in the following.

Figure 5A:
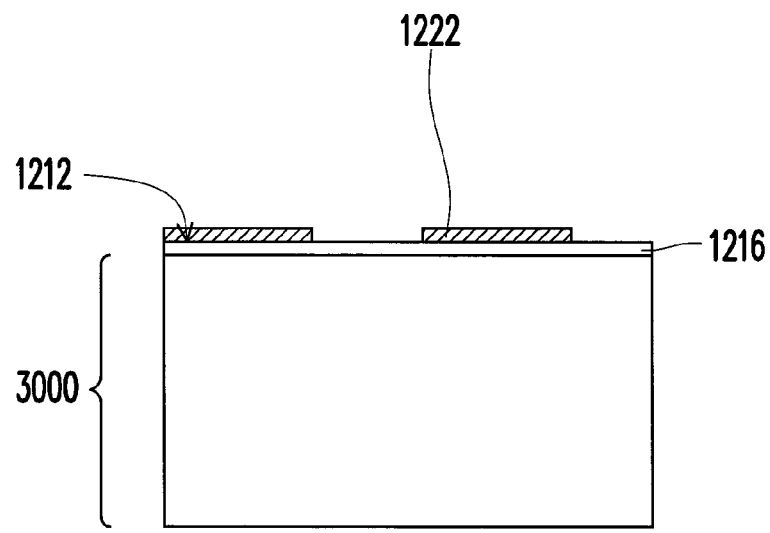
FIGS. 5A to 5F are flow charts illustrating a manufacturing process of the ultrasonic transducer detector.
Figure 5B:
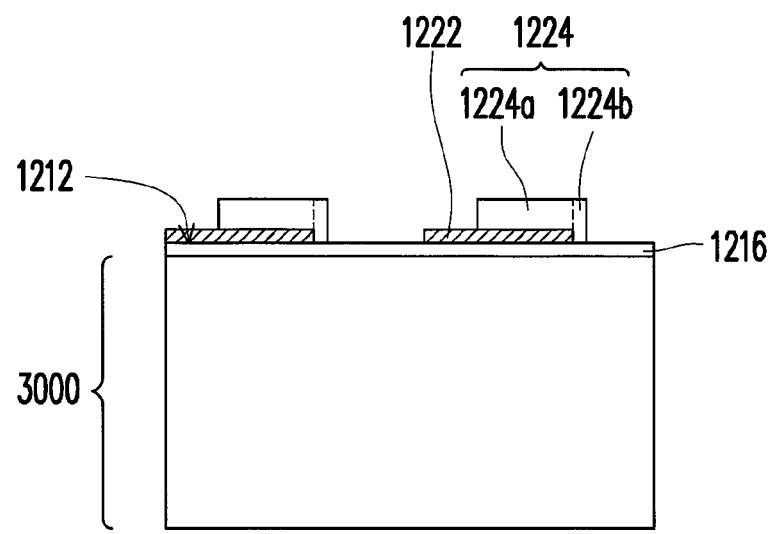
Figure 5C:
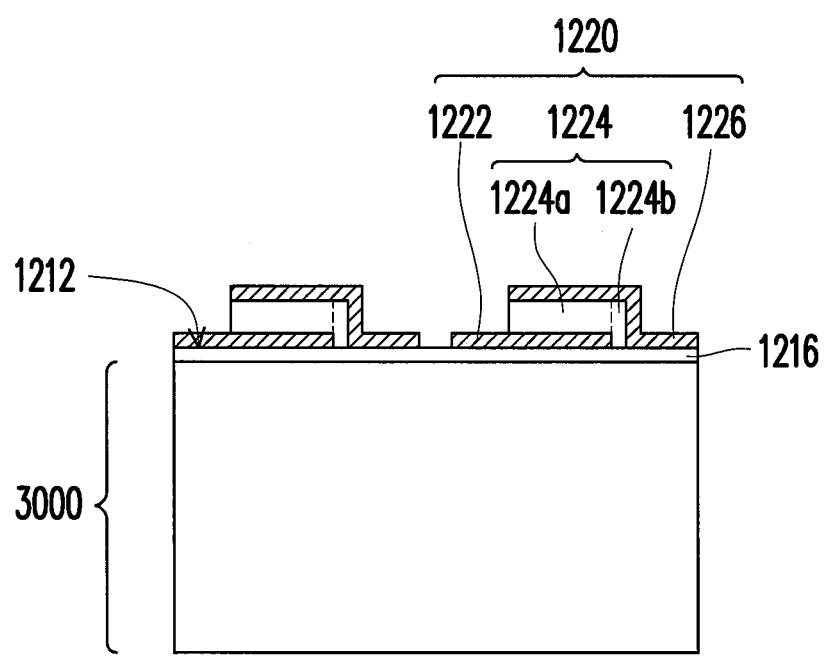
Figure 5D:
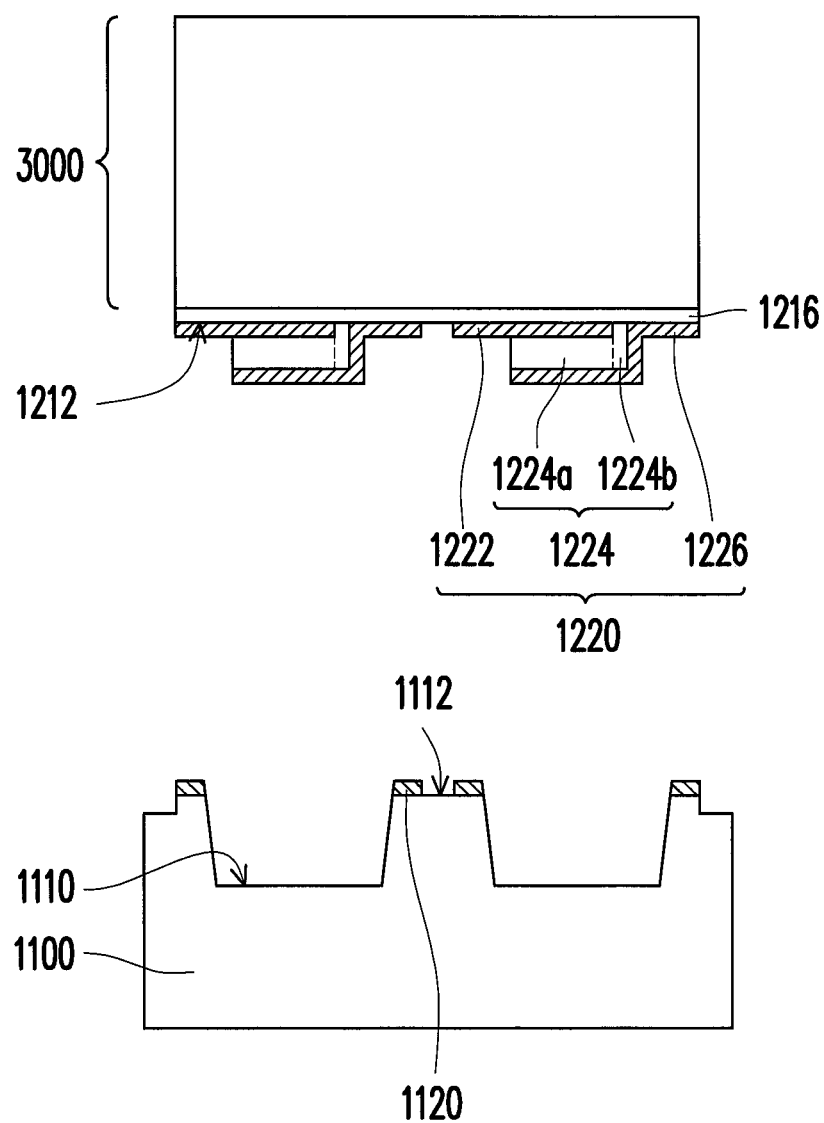
Figure 5E:
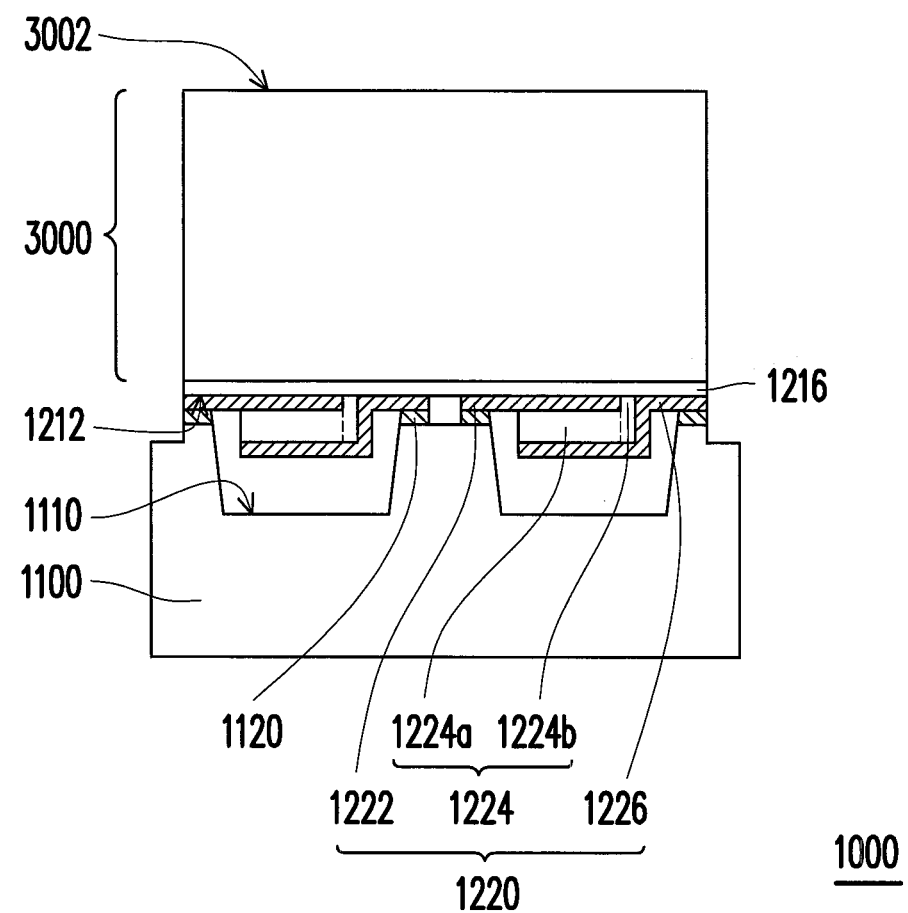
Figure 5F:
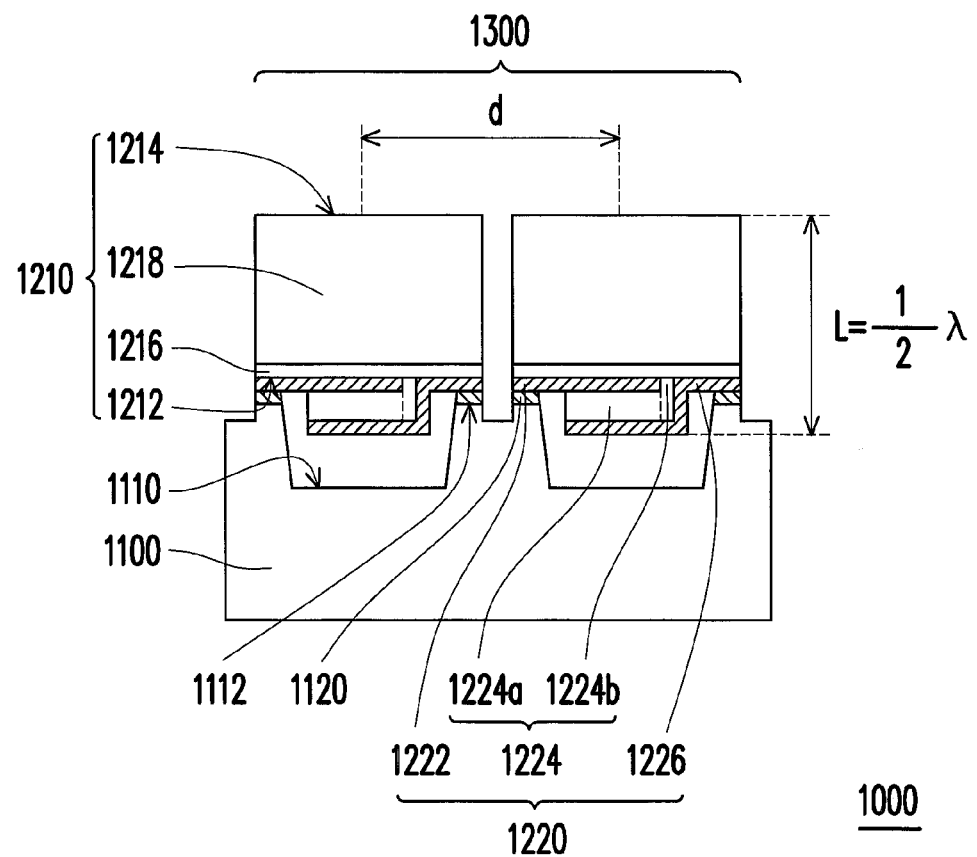

As shown in FIG. 5A, a wafer 3000 is provided, and the thickness of the wafer 3000 may be slightly greater than ½ wavelength λ of the operating frequency F. An insulating material layer is deposited on the silicon wafer 3000 to form the insulating layer 1216, and a top surface of the insulating layer 1216 is the second surface 1212. Then, the first electrode 1222 is formed on the second surface 1212. As shown in FIG. 5B, the piezoelectric material layer 1224 is formed on the second surface 1212, in which the second part 1224b of the piezoelectric material layer 1224 is formed on the second surface 1212 of the oscillating element 1210, and extending the first part 1224a to be disposed on the first electrode 1222. Next, as shown in FIG. 5C, forming the second electrode 1226 on the second surface 1212 at the part which is not covered by the first electrode 1222 and the piezoelectric material layer 1224. The first electrode 1222, the piezoelectric material layer 1224, and the second electrode 1226 form the piezoelectric element 1220. Afterward, as shown in FIG. 5D, the substrate 1100 having the semiconductor elements and the layout 1120 is provided, in which the substrate 1100 has a plurality of openings 1110 disposed on the first surface 1112. Then, as shown in FIG. 5E, the silicon wafer 3000 is correspondingly joined with the substrate 1100, and the piezoelectric element 1220 is located in the corresponding opening 1110. Next, referring to FIGS. 5E and 5F, an etching process is performed on a bottom surface 3002 of the silicon wafer 3000, so as to define the oscillating element 1210 (as shown in FIG. 3), in which the total thickness (the thickness L of the resonance unit 1200) of the oscillating element 1210 and the piezoelectric element 1220 is equivalent to ½ wavelength λ of the signal frequency F. Then, referring to FIGS. 3 and 4, when the ultrasonic transducer detector 1000 of this embodiment is used, the ultrasonic wave is transmitted from the external environment to the third surface 1214 of the oscillating element 1210, and as the thickness L of the resonance unit 1200 is equivalent to ½ wavelength λ of the signal frequency F, when the resonance of the oscillating element 1210 is initiated at the direction of the thickness, the piezoelectric element 1220 converts an elastic wave signal of the oscillating element 1210 to an electric signal, and transmits the electric signal to the substrate 1100 for processing and performing radiography.

Figure 6:
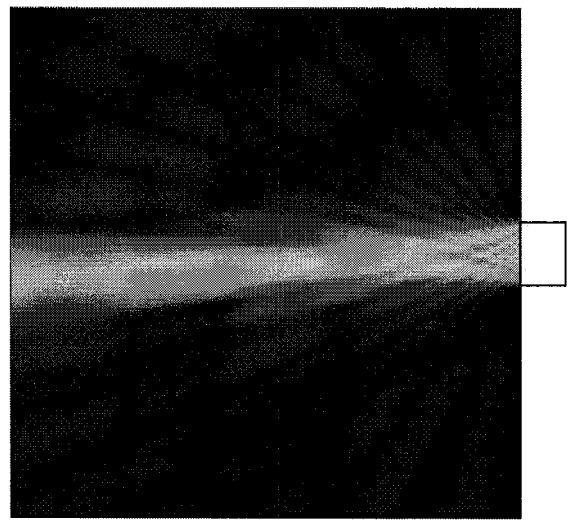
FIG. 6 is a simulated sound field diagram illustrating a pointing effect in water when the unit space of a wave source array is smaller than ½ wavelength.

In particular, the ultrasonic transducer detector 1000 in this embodiment, determines the operating frequency by the thickness. In comparison with the plane dimension of the resonance unit 1200, the thickness L of the resonance unit 1200 has more influence on determining the operating frequency. In other words, the influence of the plane dimensions of the two resonance units 1200 on determining the operating frequency F is not great. Therefore, the plane dimension of the resonance unit 1200 can be reduced without influencing the operating frequency through the lithography and etching processes applied in the manufacturing process of the semiconductor, and thus the unit space d is smaller than ½ wavelength λ, thereby effectively inhibiting the grating lobe effect and generating radiography correctly, as shown in FIG. 6. Moreover, in the manufacturing process, a larger process margin is provided for determining the plane dimension of the resonance unit 1200.

In addition, the ultrasonic transducer array 1300 is formed on the wafer, and the ultrasonic transducer array 1300 could be joined with a substrate made of the wafer with semiconductor elements on it, so that an easy joining manner for arranging high-density wires in an array is provided.

Based on the above descriptions, the ultrasonic transducer detector of the invention at least has the following advantages.

Firstly, by adopting the manner of determining the operating frequency through the thickness, reducing the plane dimension has little influence on determining the operating frequency; and meanwhile, the lithography process is performed to make the unit space of the resonance units smaller than ½ wavelength, so as to effectively inhibit the grating lobe effect and generate radiography correctly.

Secondly, by adopting the manner of determining the operating frequency through the thickness, the plane dimension of the resonance unit has a larger process margin.

Thirdly, an easy joining manner is provided for arranging high-density wires in an array.

It will be apparent to those skilled in the art that various modifications and variations can be made to the structure of the disclosed embodiments without departing from the scope or spirit of the invention. In view of the foregoing, it is intended that the invention cover modifications and variations of this invention provided they fall within the scope of the following claims and their equivalents.

What is claimed is:

1. An ultrasonic transducer detector with an operating frequency, comprising:
   a substrate, comprising a plurality of openings located on a first surface of the substrate; and
   an ultrasonic transducer array, disposed on the first surface of the substrate, and comprising at least one resonance unit, wherein the thickness of the resonance unit is equivalent to ½ wavelength of the operating frequency, each resonance unit comprising: an oscillating element, comprising a second surface corresponding to one of the openings on the first surface of the substrate; and
   a piezoelectric element, disposed on the second surface.

2. The ultrasonic transducer detector according to claim 1, wherein the substrate is a silicon substrate, and comprises a plurality of semiconductor elements and a layout.

3. The ultrasonic transducer detector according to claim 1, wherein the openings are blind holes or through holes.

4. The ultrasonic transducer detector according to claim 1, wherein each of the oscillating elements comprises an insulating layer and the second surface is the surface of the insulating layer adjacent to the substrate.

5. The ultrasonic transducer detector according to claim 1, wherein each piezoelectric element comprises:
   a first electrode, disposed on a part of the second surface of the oscillating element;
   a piezoelectric material layer, comprising a first part and a second part connected to each other, wherein the first part is disposed on the second surface of the oscillating element and located next to the first electrode, and the second part is disposed on a surface of the first electrode; and
   a second electrode, covered on a part of the second surface of the oscillating element which is exposed by the first electrode and the piezoelectric material layer, and extending to be disposed on the piezoelectric material layer.

6. The ultrasonic transducer detector according to claim 5, wherein each oscillating element further comprises a third surface adjacent to the second surface and being away from the substrate, the second electrode comprises a fourth surface adjacent to the opening, and the thickness of each resonance unit is a distance between the third surface of the oscillating element and the fourth surface of the second electrode.

7. The ultrasonic transducer detector according to claim 1, wherein the oscillating elements are columns.

8. The ultrasonic transducer detector according to claim 1, wherein the oscillating elements are made of an elastic material, and the elastic material is deformed to drive the piezoelectric element.

9. The ultrasonic transducer detector according to claim 8, wherein the elastic material comprises metal or semiconductor material.

10. The ultrasonic transducer detector according to claim 9, wherein the semiconductor material comprises silicon.

* * * * *